(12) United States Patent
Staniforth et al.

(10) Patent No.: US 6,810,875 B2
(45) Date of Patent: Nov. 2, 2004

(54) MOUTHPIECE FOR A PARTICULATE INHALER

(75) Inventors: John Nicholas Staniforth, Bath (GB); David Alexander Vodden Morton, Bath (GB); Iain Grierson McDerment, Herts (GB)

(73) Assignee: Andi-Ventis Limited, Limassol (CY)

( * ) Notice: Subject to any disclaimer, the term of this patent is extended or adjusted under 35 U.S.C. 154(b) by 39 days.

(21) Appl. No.: 10/283,418

(22) PCT Filed: May 17, 2001

(86) PCT No.: PCT/GB01/02209

§ 371 (c)(1),
(2), (4) Date: Nov. 18, 2002

(87) PCT Pub. No.: WO01/95963

PCT Pub. Date: Dec. 20, 2001

(65) Prior Publication Data

US 2003/0150452 A1 Aug. 14, 2003

(30) Foreign Application Priority Data

Jun. 12, 2000 (EP) ............................................. 00304959

(51) Int. Cl.[7] ............................................. B65D 83/06
(52) U.S. Cl. .......................... 128/203.15; 128/200.14; 128/203.12; 128/203.23; 604/58
(58) Field of Search .... 604/57–64; 128/200.14–200.24, 128/203.12, 203.15, 203.23, 207.14–207.18, 201.26, 202.21, 204.26

(56) References Cited

U.S. PATENT DOCUMENTS

| | | | |
|---|---|---|---|
| 3,795,244 A | | 3/1974 | Lax et al. |
| 5,033,463 A | * | 7/1991 | Cocozza ................. 128/203.21 |
| 6,347,629 B1 | * | 2/2002 | Braithwaite ............ 128/203.15 |
| 6,655,380 B1 | * | 12/2003 | Andersson et al. .... 128/203.15 |
| 2003/0015195 A1 | * | 1/2003 | Haaije de Boer et al. ..................... 128/203.15 |

FOREIGN PATENT DOCUMENTS

| | | |
|---|---|---|
| WO | WO 95/06491 | 8/1994 |
| WO | WO 98/41264 | 3/1998 |
| WO | WO 01/95963 | 12/2001 |

* cited by examiner

*Primary Examiner*—Glenn K. Dawson
(74) *Attorney, Agent, or Firm*—George R. McGuire; Bond, Schoeneck & King, PLLC

(57) ABSTRACT

Mouthpieces for particulate inhalers typically have either stationary particle deflectors or rotatable devices for changing the flow of particulate material through the mouthpiece. However, these mouthpieces do not prevent the build up of particulate drug on the walls of the mouthpiece. Thus, there is provided a mouthpiece (10) for use in an inhaler for particulate medicament, the mouthpiece having an inlet (12) and an outlet (13) for particulate medicament, a helical member (15) disposed between the inlet and the outlet for, in use, imparting a rotational movement to an air flow which is drawn through the mouthpiece and in which medicament is entrained, wherein the helical member (15) is, in use, axially movable between a first position and a second position such that it restricts the build up of medicament on the inside of the mouthpiece (10).

7 Claims, 2 Drawing Sheets

MOUTHPIECE FOR A PARTICULATE INHALER

CROSS REFERENCE TO RELATED APPLICATIONS

Figure 1:
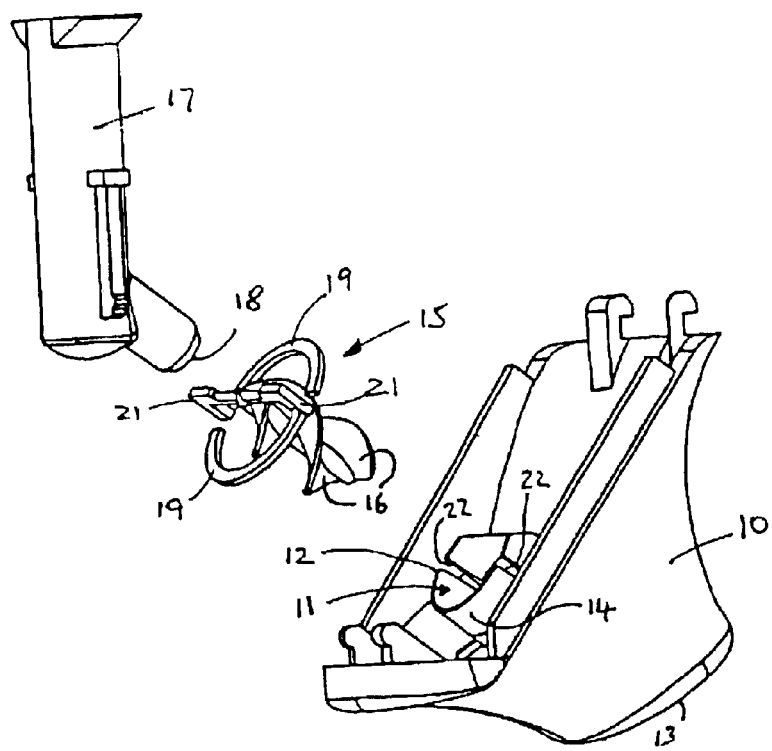
Figure 2:
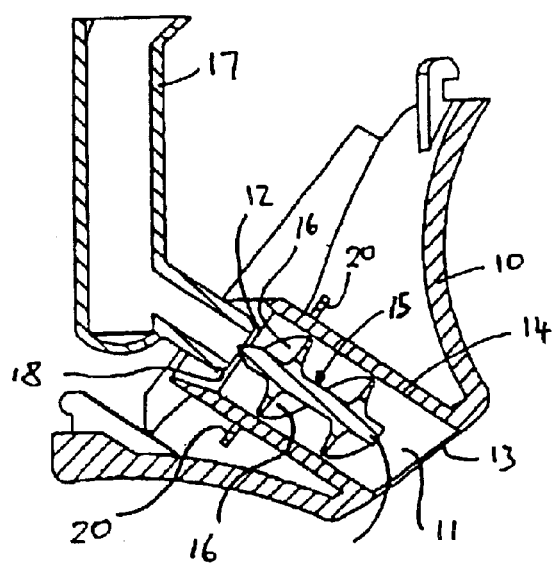
Figures 3, 4:
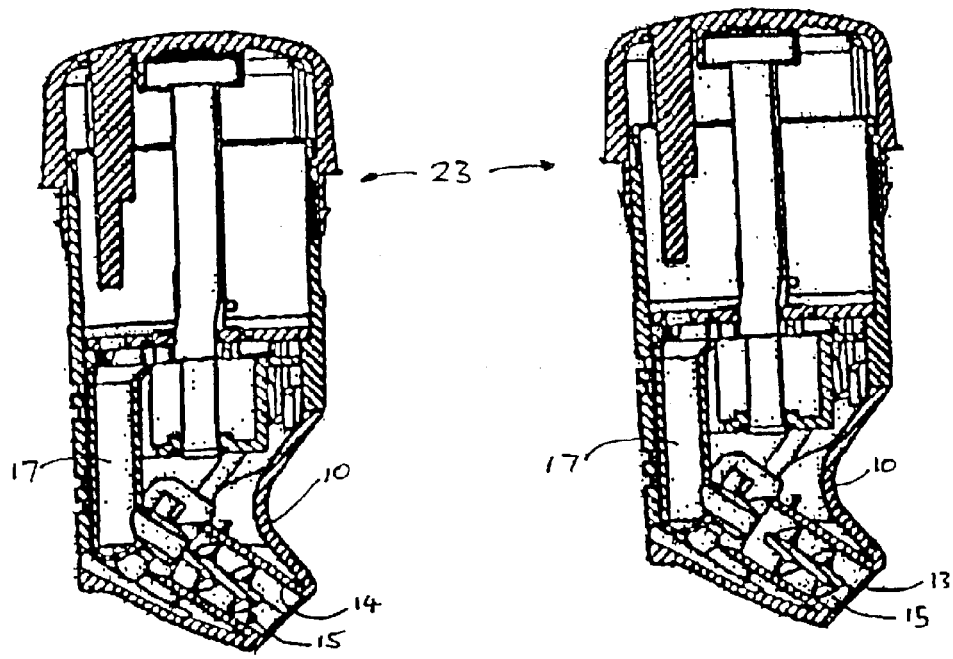

The present application is the U.S. National Stage Filing of PCT Application No. PCT/GB01/02209, filed May 17, 2001, that claims priority to European Patent Application No. 00304959.0, filed Jun. 12, 2000.

BACKGROUND OF THE INVENTION

This invention relates to particulate inhalers and, in particular, to a mouthpiece for such an inhaler, the mouthpiece being provided with means for ensuring that the particle size of the entrained medicament is minimized.

Mouthpieces for inhalers in the prior art have used many different means for breaking up the particulate medicament which is being inhaled by the patient. Such means include the use of staggered teeth, baffle plates, filters and stationary helical devices.

In particular, as disclosed in WO 98/41264, it is known to provide a rotatable member within the mouthpiece, the rotatable member having a number of angled arms with which entrained medicament may collide during operation of the inhaler.

A disadvantage with such an arrangement is that a rotatable member will spin with the air flow which reduces both surface effects and also the likelihood of any impact of the medicament with the rotatable member, as some particles can travel undeflected through the mouthpiece. The airflow causes the arms of the rotatable member to rotate out of the path of the particle and, thus the arms, rather than the particles, gain rotational energy such that the particles experience a reduced acceleration and shear. Further, a rotatable member is more susceptible to friction at the points at which it is mounted within the mouthpiece. Furthermore, the performance of the rotatable member will be adversely effected as the speed at which it rotates increases. The present invention is directed to providing a mouthpiece for use in an inhaler for particulate medicament to break up agglomerations of particles and which overcomes the above problems.

BRIEF SUMMARY OF THE INVENTION

According to the present invention, there is provided a mouthpiece for use in an inhaler for particulate medicament, the mouthpiece having:

an inlet and an outlet for particulate medicament;

a helical member disposed between the inlet and outlet for, in use, imparting a rotational movement to an air flow which is drawn to the mouthpiece and in which medicament is entrained;

wherein the helical member is, in use, axially movable between a first position and a second position such that it restricts the build up of medicament on the inside of the mouthpiece.

Thus, the helical member, which may scrape the inside of the mouthpiece or which may have its radially outermost part adjacent an inner side of the mouthpiece, clears deposits of medicament on the inside of the mouthpiece. Furthermore, as the axial movement of the helical member introduces an acceleration and a vibration to the helical member, particles which adhere to the surface of the helical member may be dislodged.

Thus, the present invention provides a non-rotating member, the performance of which is not adversely effected by loss of performance due to rotation. Thus, the present invention clears depositions of particulate medicament without sacrificing the energy which is required to rotate the rotatable member of the prior art.

Preferably, the mouthpiece further comprises biasing means for urging the helical member towards the inlet to the mouthpiece.

The biasing means may be a pair of resilient arms attached to the helical member, preferably at one end thereof.

The helical member may have a plurality of intertwined helical sections, preferably two.

Preferably, the helical sections each complete at least one revolution.

Preferably, the movement of the helical member Is caused by the airflow drawn through the mouthpiece, in use, by the user.

BRIEF DESCRIPTION OF THE SEVERAL VIEWS OF THE DRAWINGS

An embodiment of the invention will now be described with reference to the accompanying drawings in which:

FIG. 1 is an exploded perspective view of a mouthpiece according to the present invention;

FIG. 2 is a cross-sectional view through a mouthpiece according to the present invention;

FIG. 3 is a cross-sectional view through an inhaler showing the helical member in its first position;

FIG. 4 is a cross-sectional view through an inhaler showing the helical member in its second position.

DETAILED DESCRIPTION OF THE INVENTION

As can be seen from FIGS. 1 and 2, a mouthpiece 10 for an inhaler is provided with a passage 11 having an inlet 12 and an outlet 13 and bounded by a cylindrical wall 14. A helical member 15 is provided in the passage 11, the helical member having two intertwined helical sections 16, the radially outmost parts of both of which are adjacent to the inner side of the wall 14.

Projections 21 (shown only in FIG. 1) which extend radially from the helical member 15 are located within slots 22 in the wall 14. These projections 21 ensure that the helical member 15 cannot rotate as air is drawn through the mouthpiece 10 but allow it to move axially along the passage 11.

The helical member 15 is provided with a pair of resilient arms 19 (shown only in FIG. 1) which engage, in use, with flanges 20 on the outer surface of the wall 14 and bias the helical member towards its at rest position near the inlet 12.

As can be seen from all of the figures, the helical member 15 has a central core 24 which, in combination with the helical section 16 ensures that there is no direct path through the mouthpiece 10. Movement of the helical member 15 between its first and its second position clears deposits of medicament from the inner surface of the wall 14.

A drug supply means 17 having an outlet 18 is arranged, in use, to introduce particulate medicament through the inlet 12 to the passage 11 when a user of the inhaler operates the device by drawing air through the mouthpiece.

An inhaler 23 is shown In FIGS. 3 and 4, the inhaler being provided with a mouthpiece 10 of the type shown in FIGS. 1 and 2. FIG. 3 shows the helical member in a first position in which it rests at the upstream end of the passage 11 prior to the start of inhalation. During inhalation, the helical member 15 is drawn towards the downstream end (outlet) of the passage 11. The amount by which the helical member moves is dependent upon the flexibility of the resilient arms 19 and the flow rate which is achieved by the patient. Once inhalation has been completed and air Is no longer drawn through the mouthpiece 10, the resilient arms 19 urge the helical member 15 back to its at rest position near the inlet 12.

What is claimed is:

1. A mouthpiece for use in an inhaler for particulate medicament, the mouthpiece having:

an inlet and an outlet for particulate medicament; a helical member disposed between the inlet and the outlet for, in use, imparting a rotational movement to an air flow which is drawn through the mouthpiece and in which medicament is entrained;

wherein the helical member is, in use, axially movable between a first position and a second position such that it restricts the build up of medicament on the inside of the mouthpiece.

2. A mouthpiece according to claim 1, further comprising biasing means for urging the helical member towards the inlet.

3. A mouthpiece according to claim 2, wherein the biasing means is a pair of resilient arms at one end of the helical member.

4. A mouthpiece according to any one of claims 1 to 3, wherein the helical member has a plurality of intertwined helical sections.

5. A mouthpiece according to claim 4, wherein the helical member has two intertwined helical sections.

6. A mouthpiece according to either claim 4 or claim 5, wherein the helical sections each complete at least one revolution.

7. A mouthpiece according to any one of the preceding claims, wherein, in use, the movement of the helical member is caused by the air flow drawn through the mouthpiece by the user.

\* \* \* \* \*